United States Patent
Kaneko

(12) 
(10) Patent No.: US 7,851,428 B2
(45) Date of Patent: Dec. 14, 2010

(54) NORMAL PROPYL BROMIDE COMPOSITION

(75) Inventor: Akiyasu Kaneko, Saitama (JP)

(73) Assignee: Kaneko Chemical Co., Ltd., Saitama (JP)

( * ) Notice: Subject to any disclaimer, the term of this patent is extended or adjusted under 35 U.S.C. 154(b) by 377 days.

(21) Appl. No.: 11/792,992

(22) PCT Filed: Aug. 29, 2006

(86) PCT No.: PCT/JP2006/016912

§ 371 (c)(1),
(2), (4) Date: Mar. 27, 2008

(87) PCT Pub. No.: WO2007/060778

PCT Pub. Date: May 31, 2007

(65) Prior Publication Data

US 2008/0300433 A1    Dec. 4, 2008

(30) Foreign Application Priority Data

Nov. 25, 2005   (JP) .............................. 2005-340279
Aug. 22, 2006   (JP) .............................. 2006-225505

(51) Int. Cl.
*C11D 14/02*       (2006.01)
*C11D 17/00*       (2006.01)
*B01F 1/00*        (2006.01)
*C07C 17/42*       (2006.01)

(52) U.S. Cl. ...................... 510/255; 510/412; 252/364; 570/116; 570/117

(58) Field of Classification Search ................. 510/255, 510/412; 252/364; 570/116, 117
See application file for complete search history.

(56) References Cited

U.S. PATENT DOCUMENTS 5,378,736 A   1/1995  Fujiwa et al.
5,858,953 A   1/1999  Aman et al.

FOREIGN PATENT DOCUMENTS

| EP | 0459913 A2 | 12/1991 |
|----|------------|---------|
| EP | 0609004    | 8/1994  |
| EP | 2058383    | 5/2009  |
| FR | 2732963 A1 | 10/1996 |
| JP | 04-36263   | 2/1992  |
| JP | 06-220494  | 8/1994  |
| JP | 06-345858  | 12/1994 |
| JP | 08-67643   | 3/1996  |
| JP | 11-343499  | 12/1999 |

*Primary Examiner*—Jafar Parsa
(74) *Attorney, Agent, or Firm*—Harness, Dickey & Pierce, PLC

(57) ABSTRACT

To stabilize normal propyl bromide by using a novel stabilizer which is friendly to the environment.

A composition includes, relative to 100 parts by weight of normal propyl bromide, 0.1 parts by weight to 10 parts by weight of at least one stabilizer selected from the following (A) to (D): (A) 3,4-epoxycyclohexenylmethyl 3',4'-epoxycyclohexene carboxylate; (B) ε-caprolactone modified 3,4-epoxycyclohexylmethyl 3',4'-epoxycyclohexane carboxylate; (C) vinylcyclohexene monoxide; and (D) 1,2:8,9-diepoxylimonene.

4 Claims, No Drawings

NORMAL PROPYL BROMIDE COMPOSITION

TECHNICAL FIELD

The present invention relates to a normal propyl bromide composition including normal propyl bromide, and in particular to a stabilizing technology thereof.

BACKGROUND ART

Among various cleaning solvents, chlorofluorocarbon and chlorine-based solvents have been widely used heretofore. However, the use of these cleaning solvents has been regulated because of environmental problems that have risen in recent years such as the destruction of the ozone layer. Under these circumstances, a composition mainly consisting of normal propyl bromide (aka: n-propyl bromide, 1-bromopropane; hereinafter it may also be referred to simply as NPB) has been proposed as a new cleaning solvent in place of chlorofluorocarbon and chlorine-based solvents. The KB value of n-propyl bromide is about 125 which is relatively high. It is excellent at degrease cleaning and it also has a nonflammable or flame-retardant property without a flash point. Accordingly, n-propyl bromide is not considered as a hazardous material, and is safe and easy to handle. Moreover, neither fluorine-based solvents nor chlorine-based solvents are included therein at all. From these reasons, n-propyl bromide is drawing attention as being friendly to the environment at present.

However, n-propyl bromide has a disadvantage that a decomposition reaction is likely to take place which is induced by various metals such as aluminum, zinc, iron and copper. The decomposition reaction of n-propyl bromide is caused by the contact with a metal. The reaction varies according to the kind of metal, and is significant especially in the case of aluminum. The decomposition reaction progresses at a considerably slow rate at normal temperature. On the other hand, under a heated condition, the decomposition progresses in a chain reaction manner while generating hydrogen bromide, and eventually aluminum is vigorously corroded in some cases. Accordingly, in a case where n-propyl bromide is used, e.g., for cleaning various metallic components, it is necessary to stabilize n-propyl bromide so that n-propyl bromide can be prevented from corroding objects subject to cleaning and cleaning apparatuses while suppressing the decomposition reaction induced by various metals, particularly aluminum.

CROSS-REFERENCE TO RELATED APPLICATIONS

This application is based on and claims the benefit of priority to Japanese Patent Application No. 2005-340279 filed on Nov. 25, 2005 and Japanese Patent Application No. 2006-225505 filed on Aug. 22, 2006, and the contents of which are herein incorporated by reference.

DISCLOSURE OF THE INVENTION

Problems to be Solved by the Invention

Heretofore, in an attempt to stabilize n-propyl bromide, there have been disclosed methods in which nitroalkanes, ethers, epoxides or amines are added as stabilizers (refer to Patent Documents 1 and 2). However, the stabilizers proposed therein do not always exert sufficient stabilization effects on metals commonly and widely used as industrial metallic materials such as zinc, iron and copper. Particularly, in a case where the stabilizers are used under conditions at high temperatures over an extended period of time such as in vapor degreasing, the object subject to cleaning and the cleaning apparatus etc. are corroded in some cases.

Subsequently, in an attempt to sufficiently stabilize against various metals such as zinc, iron and copper, there have been proposed using, in combination as stabilizers, two or more of nitroethane or nitromethane and 1,2-butylene oxide or trimethoxymethane (refer to Patent Documents 3 to 7).

However, it has been necessary to use two or more of these stabilizers in combination. From this reason, it has been desired to develop a novel stabilizer excellent in obtaining a sufficient stabilization effect even on the various metals such as zinc, iron and copper.

The present invention has been made under these circumstances, and an object of the present invention is to stabilize n-propyl bromide compositions by using a novel stabilizer which is friendly to the environment.

Patent Document 1: JP-A 6-220494
Patent Document 2: JP-A-7-150197
Patent Document 3: JP-A 8-311675
Patent Document 4: JP-A 8-337795.
Patent Document 5: JP-A 9-302389
Patent Document 6: JP-A 11-343499
Patent Document 7: JP-A 2000-26897

Means for Solving the Problems

A main invention for achieving the above object is a normal propyl bromide composition including,
relative to 100 parts by weight of normal propyl bromide,
0.1 parts by weight to 10 parts by weight of at least one stabilizer selected from the following (A) to (D):
(A) 3,4-epoxycyclohexenylmethyl 3',4'-epoxycyclohexene carboxylate;
(B) ε-caprolactone modified 3,4-epoxycyclohexylmethyl 3',4'-epoxycyclohexane carboxylate;
(C) vinylcyclohexene monoxide; and
(D) 1,2:8,9-diepoxylimonene
Other features of the present invention will be made clear from the description of the present specification and appended drawings.

BEST MODES FOR CARRYING OUT THE INVENTION

According to the description of the present specification and appended drawings, the following points will at least be made clear.

A normal propyl bromide composition includes, relative to 100 parts by weight of normal propyl bromide,
0.1 parts by weight to 10 parts by weight of at least one stabilizer selected from the following (A) to (D):
(A) 3,4-epoxycyclohexenylmethyl 3',4'-epoxycyclohexene carboxylate;
(B) ε-caprolactone modified 3,4-epoxycyclohexylmethyl 3',4'-epoxycyclohexane carboxylate;
(C) vinylcyclohexene monoxide
(1,2-epoxy-4-vinylcyclohexane); and
(D) 1,2:8,9-diepoxylimonene.
With this n-propyl bromide composition, it is possible to sufficiently stabilize n-propyl bromide by, use of the stabilizers (A) to (D).

A normal propyl bromide composition includes, relative to 100 parts by weight of normal propyl bromide:

0.01 parts by weight to 10 parts by weight of at least one stabilizer selected from nitromethane, nitroethane, 1,3-dioxolane, trimethoxymethane, 1,1,1-trimethoxyethane and 1,2-butylene oxide; and 0.05 parts by weight to 10 parts by weight of at least one stabilizer selected from the following (A) to (D):

(A) 3,4-epoxycyclohexenylmethyl 3',4'-epoxycyclohexene carboxylate;

(B) ε-caprolactone modified 3,4-epoxycyclohexylmethyl 3',4'-epoxycyclohexane carboxylate;

(C) vinylcyclohexene monoxide (1,2-epoxy-4-vinylcyclohexane); and (D) 1,2:8,9-diepoxylimonene.

With this n-propyl bromide composition, it is possible to sufficiently stabilize n-propyl bromide by use of the stabilizers (A) to (D).

A normal propyl bromide composition includes, relative to 100 parts by weight of normal propyl bromide: 0.01 parts by weight to 10 parts by weight of at least either one stabilizer of nitromethane and nitroethane; and 0.05 parts by weight to 10 parts by weight of at least one stabilizer selected from the following (A) to (D):

(A) 3,4-epoxycyclohexenylmethyl 3',4'-epoxycyclohexene carboxylate;

(B) ε-caprolactone modified 3,4-epoxycyclohexylmethyl 3',4'-epoxycyclohexane carboxylate;

(C) vinylcyclohexene monoxide (1,2-epoxy-4-vinylcyclohexane); and (D) 1,2:8,9-diepoxylimonene.

With this n-propyl bromide composition, it is possible to sufficiently stabilize n-propyl bromide by use of the stabilizers (A) to (D).

A normal propyl bromide composition includes, relative to 100 parts by weight of normal propyl bromide:

0.1 parts by weight to 10 parts by weight of at least either one stabilizer of nitromethane and nitroethane;

0.1 parts by weight to 10 parts by weight of at least one stabilizer selected from 1,3-dioxolane, trimethoxymethane, 1,1,1-trimethoxyethane and 1,2-butylene oxide; and 0.005 parts by weight to 10 parts by weight of at least one stabilizer selected from the following (A) to (D):

(A) 3,4-epoxycyclohexenylmethyl 3',4'-epoxycyclohexene carboxylate;

(B) ε-caprolactone modified 3,4-epoxycyclohexylmethyl 3',4'-epoxycyclohexane carboxylate;

(C) vinylcyclohexene monoxide; and (D) 1,2:8,9-diepoxylimonene.

With this n-propyl bromide composition, it is possible to sufficiently stabilize n-propyl bromide by including: nitromethane or nitroethane; 1,3-dioxolane, trimethoxymethane, 1,1,1-trimethoxyethane or 1,2-butylene oxide; and the above-described stabilizers (A) to (D).

Overview of Normal Propyl Bromide Composition

The n-propyl bromide composition according to the present invention is characterized by including, relative to 100 parts by weight of normal propyl bromide, 0.1 parts by weight to 10 parts by weight of at least one stabilizer selected from the following (A) to (D):

(A) 3,4-epoxycyclohexenylmethyl 3',4'-epoxycyclohexene carboxylate;

(B) ε-caprolactone modified 3,4-epoxycyclohexylmethyl 3',4'-epoxycyclohexane carboxylate;

(C) vinylcyclohexene monoxide (1,2-epoxy-4-vinylcyclohexane); and (D) 1,2:8,9-diepoxylimonene (1,2,8,9-diepoxylimonene).

In the n-propyl bromide composition, these stabilizers (A) to (D) may be included singly, or two or more of these may be included in combination. By including these stabilizers (A) to (D) in the n-propyl bromide composition, it is possible to sufficiently suppress the decomposition reaction caused by the contact between the n-propyl bromide and metal, and to reduce the generation of hydrogen bromide. Therefore, it is possible to use the n-propyl bromide composition for, e.g., cleaning various metallic components.

Furthermore, the amount of these stabilizers (A) to (D) to be included is set to 0.1 parts by weight to 10 parts by weight based on the following reason. That is because, in a case where the amount of these stabilizers (A) to (D) to be included is less than 0.1 parts by weight, a sufficient stabilization effect on n-propyl bromide is not confirmed. Meanwhile, in a case where the amount of the stabilizers (A) to (D) to be included exceeds 10 parts by weight, there is no problem regarding the stabilization effect itself, but no additional effects can be expected, and so this would not be economical.

Moreover, another n-propyl bromide composition according to the present invention is characterized by including, relative to 100 parts by weight of n-propyl bromide:

0.05 parts by weight to 10 parts by weight of at least one stabilizer selected from nitromethane, nitroethane, 1,3-dioxolane, trimethoxymethane, 1,1,1-tri ethoxyethane and 1,2-butylene oxide; and 0.05 parts by weight to 10 parts by weight of at least one stabilizer selected from the above-described (A) to (D)

In the n-propyl bromide composition, these stabilizers (A) to (D) may be included singly, or two or more of these may be included in combination. Moreover, nitromethane, nitroethane, 1,3-dioxolane, trimethoxymethane, 1,1,1-trimethoxyethane and 1,2-butylene oxide may also be included singly, or two or more of these may be included in combination, likewise.

By using these stabilizers (A) to (D) and nitromethane, nitroethane, 1,3-dioxolane, trimethoxymethane, 1,1,1-trimethoxyethane or 1,2-butylene oxide in combination, it is possible to more sufficiently suppress the decomposition reaction caused by the contact between n-propyl bromide and metal, and to reduce the generation of hydrogen bromide. Therefore, it is possible to use the n-propyl bromide composition for, e.g., cleaning various metallic components.

Furthermore, another n-propyl bromide composition according to the present invention is characterized by including, relative to 100 parts by weight of n-propyl bromide:

0.01 parts by weight to 10 parts by weight of at least either one stabilizer of nitromethane and nitroethane; and 0.05 parts by weight to 10 parts by weight of at least one stabilizer selected from the above-described (A) to (D).

Note that, in the n-propyl bromide composition according to the present invention, other types of stabilizers may be included in addition to the aforementioned stabilizers (A) to (D), nitromethane, nitroethane, 1,3-dioxolane, trimethoxymethane, 1,1,1-trimethoxyethane and 1,2-butylene oxide.

Still furthermore, another n-propyl bromide composition according to the present invention is characterized by including, relative to 100 parts by weight of n-propyl bromide:

0.1 parts by weight to 10 parts by weight of at least either one stabilizer of nitromethane and nitroethane;

0.1 parts by weight to 10 parts by weight of at least one stabilizer selected from 1,3-dioxolane, trimethoxymethane, 1,1,1-trimethoxyethane and 1,2-butylene oxide; and 0.005 parts by weight to 10 parts by weight of at least one stabilizer selected from the above-described (A) to (D).

In this respect, either one of nitromethane and nitroethane may be included singly, or both may be included together. Moreover, 1,3-dioxolane, trimethoxymethane, 1,1,1-trimethoxyethane and 1,2-butylene oxide may be included singly, or two or more of these may be included in combination. Moreover, in the n-propyl bromide composition, the above-described stabilizers (A) to (D) may be included singly, or two or more of these may be included in combination.

By including: nitromethane or nitroethane; 1,3-dioxolane, trimethoxymethane, 1,1,1-trimethoxyethane or 1,2-butylene oxide; and the above-described stabilizers (A) to (D), it is possible to more sufficiently suppress the decomposition reaction caused by the contact between n-propyl bromide and metal, and to reduce the generation of hydrogen bromide. Furthermore, in a case where the cleaning solvent is used repeatedly in vapor degreasing, for example, it is possible to prevent the occurrence of defects such as the generation of rust on metallic components or the like.

Note that, in the n-propyl bromide composition according to the present invention, other types of stabilizers may be included in addition to the aforementioned stabilizers (A) to (D), nitromethane, nitroethane, 1,3-dioxolane, trimethoxymethane, 1,1,1-trimethoxyethane and 1,2-butylene oxide.

Stabilizers

Here, description will be given of the stabilizers (A) to (D) included in the n-propyl bromide composition according to the present invention. These stabilizers (A) to (D) are epoxy compounds using peracetic acid, and are compounds with a small content of chlorine, sodium, or the like, since epichlorohydrin is not used. Each of these stabilizers (A) to (D) will be described in detail below.

(A) 3,4-epoxycyclohexenylmethyl 3',4'-epoxycyclohexene carboxylate [(3'-4'-Epoxycyclohexane)methyl 3'-4'-Epoxycyclohexyl-carboxylate]

This compound (hereinafter may be referred to as stabilizer (A)) is a compound with a molecular weight of 252.3 and CAS number "2386-87-0", and is provided, for example, from DAICEL CHEMICAL INDUSTRIES LTD. as "CELLOXIDE 2021P (CEL2021)" (product name). This compound is an alicyclic epoxy resin manufactured by an epoxidation technique using peracetic acid, is in a liquid form with low viscosity, and does not include halogen impurities such as chlorine.

(B) ε-caprolactone modified 3,4-epoxycyclohexylmethyl 3',4'-epoxycyclohexane carboxylate [(3'-4'-Epoxycyclohexane)methyl 3'-4'-Epoxycyclohexyl-carboxylate modified ε-caprolactone]

This compound (hereinafter may be referred to as stabilizer (B)) is provided, for example, from DAICEL CHEMICAL INDUSTRIES LTD. as "CELLOXIDE 2081 (CEL2081)" (product name).

(C) Vinylcyclohexene monoxide (1,2-epoxy-4-vinylcyclohexane) (Vinylcyclohexene monoxide, 1,2-epoxy-4-vinylcyclohexane)

This compound (hereinafter may be referred to as stabilizer (C)) is a compound with a molecular weight of 124.18 and CAS number "106-86-5." This compound is provided, for example, from DAICEL CHEMICAL INDUSTRIES LTD. as "CELLOXIDE 2000 (CEL2000)" (product name).

The structure of this compound is shown below.

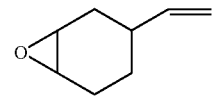

Vinylcyclohexene monoxide
(1,2-epoxy-4-vinylcyclohexane)

(D) 1,2:8,9-diepoxylimonene (1,2:8,9 Diepoxylimonen) "aka: 1-methyl-4-(2-methyloxiranyl)-7-oxabicyclo[4.1.0] heptane"

This compound (hereinafter may be referred to as stabilizer (D)) is an alicyclic diepoxy compound with CAS number "96-08-2."

This compound is provided, for example, from DAICEL CHEMICAL INDUSTRIES LTD. as "CELLOXIDE 3000 (CEL3000)" (product name).

The structure of this compound is shown below.

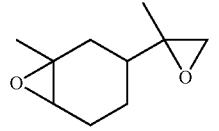

1,2 : 8,9-diepoxylimonene

Usage

The main usage of this n-propyl bromide composition can include a resist stripper, a flux cleaner, a degreasing cleaner for fats and oils etc., a buff cleaner, a resolvent for adhesives (urethane, epoxy, silicon or the like), a dry cleaning solvent, a remover for grease, oil, wax, ink or the like, a coating solvent, an extractant, a cleaner for various materials made of glass, ceramic, rubber and metal and particularly IC components, electric devices, precision devices, optical lenses or the like, and a draining agent.

Moreover, in a case where the n-propyl bromide composition is used as a cleaning solvent, it can be used in various cleaning methods such as hand wash, immersion, spray, ultrasonic cleaning, vapor degreasing, nozzle cleaning of loading apparatus for adhesives (urethane, epoxy, silicon or the like), or other general cleaning.

Stabilization Confirmation Test

<Test 1>

Description will be given of a stabilization test of n-propyl bromide by the stabilizers (A) to (D) used herein. In this test, a confirmation test was performed on stabilization effects of the stabilizers (A) to (D) previously described which are used in the n-propyl bromide composition according to the present invention and conventionally-used stabilizers etc. As the conventionally-used stabilizers etc., nitroethane, nitromethane, 1,3-dioxolane, 1,2-butylene oxide, trimethoxymethane, 1,1, 1-trimethoxyethane and limonene were used.

Moreover, as the stabilizer (A) [3,4-epoxycyclohexenylmethyl 3',4'-epoxycyclohexene carboxylate], "CELLOXIDE 2021P (CEL2021)" (product name) of DAICEL CHEMICAL INDUSTRIES LTD. was used. Moreover, as the stabilizer (B) [ε-caprolactone modified 3,4-epoxycyclohexylmethyl 3',4'-epoxycyclohexane carboxylate], "CELLOXIDE 2081 (CEL2081)" (product name) of DAICEL CHEMICAL INDUSTRIES LTD. was used. Moreover, as the stabilizer (C) {vinylcyclohexene monoxide (1,2-epoxy-4-vinylcyclohexane)}, "CELLOXIDE 2000 (CEL2000)" (product name) of DAICEL CHEMICAL INDUSTRIES LTD. was used. Moreover, as the stabilizer (D) [1,2:8,9-diepoxylimonene], "CELLOXIDE 3000 (CEL3000)" (product name) of DAICEL CHEMICAL INDUSTRIES LTD. was used.

3 parts by weight of these stabilizers (A) to (D) and the conventionally-used stabilizers etc. were respectively mixed to 100 parts by weight of n-propyl bromide, to prepare test solutions "A1" to "A11." Then, 50 ml of the prepared test solutions were respectively poured into 100 ml glass Erlenmeyer flasks, and aluminum specimens (specification: JIS A-1100P, dimension: 13 mm×65 mm×3 mm), whose surfaces were well polished and which were cleaned and dried sufficiently, were respectively placed therein so as to extend over both the gaseous and liquid phases. Subsequently, a reflux condenser was attached to the top portion of the Erlenmeyer flask, and the solution was heated up to the boiling point on a hot water bath and refluxed while bringing the specimen into contact with both the gaseous and liquid phases. A pH test paper was attached to the reflux condenser. After heat-refluxing for 140 hours, the solution was cooled to room temperature, the specimen was taken out, and then the corrosion condition and coloring condition of the liquid phase were observed. Furthermore, the generated acidic gases were confirmed by the pH test paper.

Table 1 is the summary of the test results. Note that, the criterion for the condition of the aluminum specimen is set as "o; no change at all" and "x; luster is reduced." Moreover, the criterion for the condition of the test solution is set as "o; colorless and transparent" and "x; colored." Moreover, the presence or absence of the acidic gas generation is set as "o; no generation" and "x; presence of generation."

TABLE 1

Confirmation Test for Stabilization Effects of Stabilizers (A) to (D)

|   |   | adding amount (part by weight) | specimen condition | test solution condition | presence/ absence of gas generation |
|---|---|---|---|---|---|
| A1 | nitroethane | 3 | ○ | ○ | X |
| A2 | nitromethane | 3 | ○ | ○ | X |
| A3 | 1,2-butylene oxide | 3 | X | X | ○ |
| A4 | 1,3-dioxolane | 3 | X | X | ○ |
| A5 | trimethoxymethane | 3 | X | X | ○ |
| A6 | 1,1,1-trimethoxyethane | 3 | X | X | ○ |
| A7 | limonene | 3 | X | X | X |
| A8 | stabilizer (A) | 3 | ○ | ○ | ○ |
| A9 | stabilizer (B) | 3 | ○ | ○ | ○ |
| A10 | stabilizer (C) | 3 | ○ | ○ | ○ |
| A11 | stabilizer (D) | 3 | ○ | ○ | ○ |

As shown in Table 1, as for the test solutions "A1" and "A2" using nitroethane and nitromethane, respectively, the conditions of the specimens and test solutions were favorable, but acidic gases were generated, and so it was confirmed that the single use of nitroethane or nitromethane was difficult. Meanwhile, as for the test solutions "A3" to "A6" using 1,2-butylene oxide, 1,3-dioxolane, trimethoxymethane and 1,1,1-trimethoxyethane, respectively, the luster of the specimens was reduced and coloring of the test solutions occurred, but generation of acidic gases was not observed. In any case, it was confirmed that the single use of 1,2-butylene oxide, 1,3-dioxolane, trimethoxymethane and 1,1,1-trimethoxyethane was difficult, respectively. Meanwhile, as for the test solution "A7" using limonene, the conditions of the specimen and test solution were poor and acidic gases were generated, and so it was confirmed that the use as a stabilizer was difficult.

In contrast, as for the test solutions "A8" to "A11" using the stabilizers (A) to (D), respectively, both conditions of the specimens and test solutions were favorable and generation of acidic gases was not observed, and so it was determined that each of the stabilizers (A) to (D) is adequate for being used singly.

<Test 2>

Next, a test was performed for examining mixing amounts of the stabilizers (A) to (D). In this test, relative to 100 parts by weight of n-propyl bromide, the mixing amount of each of the stabilizers (A) to (D) was set within a range of 0.001 parts by weight to 10 parts by weight, to prepare test solutions. Then, 50 ml of the prepared test solutions were respectively poured into 100 ml glass Erlenmeyer flasks, and the same test was performed as the aforementioned test: the conditions of the aluminum specimens and the test solutions were respectively examined, and also the presence or absence of acidic gas generation was examined. As the stabilizers (A) to (D), "CELLOXIDE 2021P (CEL2021)" (product name), "CELLOXIDE 2081 (CEL2081)" (product name), "CELLOXIDE 2000 (CEL2000)" (product name) and "CELLOXIDE 3000 (CEL3000)" (product name) of DAICEL CHEMICAL INDUSTRIES LTD. were used, respectively.

Table 2 is the summary of the test results. Note that, the criterion for the condition of the aluminum specimen is set as "o; no change at all" and "x; luster is reduced." Moreover, the criterion for the condition of the test solution is set as "o; colorless and transparent" and "x; colored." Moreover, the presence or absence of the acidic gas generation is set as "o; no generation" and "x; presence of generation."

TABLE 2

Test of Examining Appropriate Mixing Amounts of Stabilizers (A) to (D)

| adding amount (part by weight) | stabilizer (A) | | | stabilizer (B) | | | stabilizer (C) | | | stabilizer (D) | | |
|---|---|---|---|---|---|---|---|---|---|---|---|---|
| | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.001 | X | X | X | X | X | X | X | X | X | X | X | X |
| 0.005 | X | X | X | X | X | X | X | X | X | X | X | X |
| 0.01 | X | X | X | X | X | X | X | X | X | X | X | X |
| 0.05 | X | X | X | X | X | X | X | X | X | X | X | X |
| 0.08 | X | X | X | X | X | X | X | X | X | X | X | X |

TABLE 2-continued

Test of Examining Appropriate Mixing Amounts of Stabilizers (A) to (D)

| adding amount (part by weight) | stabilizer (A) | | | stabilizer (B) | | | stabilizer (C) | | | stabilizer (D) | | |
|---|---|---|---|---|---|---|---|---|---|---|---|---|
| | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.1 | ◯ | ◯ | ◯ | ◯ | ◯ | ◯ | ◯ | ◯ | ◯ | ◯ | ◯ | ◯ |
| 0.3 | ◯ | ◯ | ◯ | ◯ | ◯ | ◯ | ◯ | ◯ | ◯ | ◯ | ◯ | ◯ |
| 0.5 | ◯ | ◯ | ◯ | ◯ | ◯ | ◯ | ◯ | ◯ | ◯ | ◯ | ◯ | ◯ |
| 0.8 | ◯ | ◯ | ◯ | ◯ | ◯ | ◯ | ◯ | ◯ | ◯ | ◯ | ◯ | ◯ |
| 1 | ◯ | ◯ | ◯ | ◯ | ◯ | ◯ | ◯ | ◯ | ◯ | ◯ | ◯ | ◯ |
| 3 | ◯ | ◯ | ◯ | ◯ | ◯ | ◯ | ◯ | ◯ | ◯ | ◯ | ◯ | ◯ |
| 5 | ◯ | ◯ | ◯ | ◯ | ◯ | ◯ | ◯ | ◯ | ◯ | ◯ | ◯ | ◯ |
| 8 | ◯ | ◯ | ◯ | ◯ | ◯ | ◯ | ◯ | ◯ | ◯ | ◯ | ◯ | ◯ |
| 10 | ◯ | ◯ | ◯ | ◯ | ◯ | ◯ | ◯ | ◯ | ◯ | ◯ | ◯ | ◯ |

As shown in Table 2, in a case where the mixing amount of each of the stabilizers (A) to (D) was set to 0.001 parts by weight to 0.08 parts by weight relative to 100 parts by weight of n-propyl bromide, the conditions of the specimens and test solutions were poor and generation of acidic gases was observed, and so it was determined that a sufficient stabilization effect was not imparted to n-propyl bromide. On the other hand, in a case where 0.1 parts by weight or more of each of the stabilizers (A) to (D) was mixed relative to 100 parts by weight of n-propyl bromide, the conditions of the specimens and test solutions were favorable and generation of acidic gases was not observed, and so it was determined that a sufficient stabilization effect was imparted to n-propyl bromide.

<Test 3>

Next, a test was performed by further mixing nitromethane, nitroethane, 1,3-dioxolane, trimethoxymethane, 1,1,1-trimethoxyethane and 1,2-butylene oxide in addition to the stabilizers (A) to (D). In this test, relative to 100 parts by weight of n-propyl bromide, each of the stabilizers (A) to (D) was mixed within a mixing-amount range of 0.01 parts by weight to 10 parts by weight, and the mixing amount of nitromethane, nitroethane, 1,3-dioxolane, trimethoxymethane, 1,1,1-trimethoxyethane or 1,2-butylene oxide was set to 3 parts by weight, to prepare test solutions. Then, 50 ml of the prepared test solutions were respectively poured into 100 ml glass Erlenmeyer flasks, and the same test was performed as the aforementioned test: the conditions of the aluminum specimens and the test solutions were respectively examined, and also the presence or absence of acidic gas generation was examined. As the stabilizers (A) to (D), "CELLOXIDE 2021P (CEL2021)" (product name), "CELLOXIDE 2081 (CEL2081)" (product name), "CELLOXIDE 2000 (CEL2000)" (product name) and "CELLOXIDE 3000 (CEL3000)" (product name) of DAICEL CHEMICAL INDUSTRIES LTD. were used, respectively.

Table 3 to Table 8 are the summaries of these test results. Note that, the criterion for the condition of the aluminum specimen is set as "o; no change at all" and "x; luster is reduced." Moreover, the criterion for the condition of the test solution is set as "o; colorless and transparent" and "x; colored." Moreover, the presence or absence of the acidic gas generation is set as "o; no generation" and "x; presence of generation."

TABLE 3

Confirmation Test for Stabilization Effects of Mixing with Nitroethane

| nitroethane | | stabilizer (A) | | | stabilizer (B) | | | stabilizer (C) | | | stabilizer (D) | | |
|---|---|---|---|---|---|---|---|---|---|---|---|---|---|
| adding amount (part by weight) | adding amount (part by weight) | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 3 | 0.01 | ◯ | ◯ | X | ◯ | ◯ | X | ◯ | ◯ | X | ◯ | ◯ | X |
| 3 | 0.03 | ◯ | ◯ | X | ◯ | ◯ | X | ◯ | ◯ | X | ◯ | ◯ | X |
| 3 | 0.05 | ◯ | ◯ | ◯ | ◯ | ◯ | ◯ | ◯ | ◯ | ◯ | ◯ | ◯ | ◯ |
| 3 | 0.08 | ◯ | ◯ | ◯ | ◯ | ◯ | ◯ | ◯ | ◯ | ◯ | ◯ | ◯ | ◯ |
| 3 | 0.1 | ◯ | ◯ | ◯ | ◯ | ◯ | ◯ | ◯ | ◯ | ◯ | ◯ | ◯ | ◯ |
| 3 | 0.3 | ◯ | ◯ | ◯ | ◯ | ◯ | ◯ | ◯ | ◯ | ◯ | ◯ | ◯ | ◯ |
| 3 | 0.5 | ◯ | ◯ | ◯ | ◯ | ◯ | ◯ | ◯ | ◯ | ◯ | ◯ | ◯ | ◯ |
| 3 | 0.8 | ◯ | ◯ | ◯ | ◯ | ◯ | ◯ | ◯ | ◯ | ◯ | ◯ | ◯ | ◯ |
| 3 | 1 | ◯ | ◯ | ◯ | ◯ | ◯ | ◯ | ◯ | ◯ | ◯ | ◯ | ◯ | ◯ |
| 3 | 3 | ◯ | ◯ | ◯ | ◯ | ◯ | ◯ | ◯ | ◯ | ◯ | ◯ | ◯ | ◯ |
| 3 | 5 | ◯ | ◯ | ◯ | ◯ | ◯ | ◯ | ◯ | ◯ | ◯ | ◯ | ◯ | ◯ |
| 3 | 8 | ◯ | ◯ | ◯ | ◯ | ◯ | ◯ | ◯ | ◯ | ◯ | ◯ | ◯ | ◯ |
| 3 | 10 | ◯ | ◯ | ◯ | ◯ | ◯ | ◯ | ◯ | ◯ | ◯ | ◯ | ◯ | ◯ |

TABLE 4

Confirmation Test for Stabilization Effects of Mixing with Nitromethane

| nitromethane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 3 | 0.01 | ○ | ○ | X | ○ | ○ | X | ○ | ○ | X | ○ | ○ | X |
| 3 | 0.03 | ○ | ○ | X | ○ | ○ | X | ○ | ○ | X | ○ | ○ | X |
| 3 | 0.05 | ○ | ○ | ○ | ○ | ○ | ○ | ○ | ○ | ○ | ○ | ○ | ○ |
| 3 | 0.08 | ○ | ○ | ○ | ○ | ○ | ○ | ○ | ○ | ○ | ○ | ○ | ○ |
| 3 | 0.1 | ○ | ○ | ○ | ○ | ○ | ○ | ○ | ○ | ○ | ○ | ○ | ○ |
| 3 | 0.3 | ○ | ○ | ○ | ○ | ○ | ○ | ○ | ○ | ○ | ○ | ○ | ○ |
| 3 | 0.5 | ○ | ○ | ○ | ○ | ○ | ○ | ○ | ○ | ○ | ○ | ○ | ○ |
| 3 | 0.8 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 3 | 3 | ○ | ○ | ○ | ○ | ○ | ○ | ○ | ○ | ○ | ○ | ○ | ○ |
| 3 | 5 | ○ | ○ | ○ | ○ | ○ | ○ | ○ | ○ | ○ | ○ | ○ | ○ |
| 3 | 8 | ○ | ○ | ○ | ○ | ○ | ○ | ○ | ○ | ○ | ○ | ○ | ○ |
| 3 | 10 | ○ | ○ | ○ | ○ | ○ | ○ | ○ | ○ | ○ | ○ | ○ | ○ |

TABLE 5

Confirmation Test for Stabilization Effects of Mixing with 1,3-dioxolane

| 1,3-dioxolane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 3 | 0.01 | X | X | ○ | X | X | ○ | X | X | ○ | X | X | ○ |
| 3 | 0.03 | X | X | ○ | X | X | ○ | X | X | ○ | X | X | ○ |
| 3 | 0.05 | ○ | ○ | ○ | ○ | ○ | ○ | ○ | ○ | ○ | ○ | ○ | ○ |
| 3 | 0.08 | ○ | ○ | ○ | ○ | ○ | ○ | ○ | ○ | ○ | ○ | ○ | ○ |
| 3 | 0.1 | ○ | ○ | ○ | ○ | ○ | ○ | ○ | ○ | ○ | ○ | ○ | ○ |
| 3 | 0.3 | ○ | ○ | ○ | ○ | ○ | ○ | ○ | ○ | ○ | ○ | ○ | ○ |
| 3 | 0.5 | ○ | ○ | ○ | ○ | ○ | ○ | ○ | ○ | ○ | ○ | ○ | ○ |
| 3 | 0.8 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 3 | 3 | ○ | ○ | ○ | ○ | ○ | ○ | ○ | ○ | ○ | ○ | ○ | ○ |
| 3 | 5 | ○ | ○ | ○ | ○ | ○ | ○ | ○ | ○ | ○ | ○ | ○ | ○ |
| 3 | 8 | ○ | ○ | ○ | ○ | ○ | ○ | ○ | ○ | ○ | ○ | ○ | ○ |
| 3 | 10 | ○ | ○ | ○ | ○ | ○ | ○ | ○ | ○ | ○ | ○ | ○ | ○ |

TABLE 6

Confirmation Test for Stabilization Effects of Mixing with Trimethoxymethane

| trimethoxy-methane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 3 | 0.01 | X | X | ○ | X | X | ○ | X | X | ○ | X | X | ○ |
| 3 | 0.03 | X | X | ○ | X | X | ○ | X | X | ○ | X | X | ○ |
| 3 | 0.05 | ○ | ○ | ○ | ○ | ○ | ○ | ○ | ○ | ○ | ○ | ○ | ○ |
| 3 | 0.08 | ○ | ○ | ○ | ○ | ○ | ○ | ○ | ○ | ○ | ○ | ○ | ○ |
| 3 | 0.1 | ○ | ○ | ○ | ○ | ○ | ○ | ○ | ○ | ○ | ○ | ○ | ○ |
| 3 | 0.3 | ○ | ○ | ○ | ○ | ○ | ○ | ○ | ○ | ○ | ○ | ○ | ○ |
| 3 | 0.5 | ○ | ○ | ○ | ○ | ○ | ○ | ○ | ○ | ○ | ○ | ○ | ○ |
| 3 | 0.8 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 3 | 3 | ○ | ○ | ○ | ○ | ○ | ○ | ○ | ○ | ○ | ○ | ○ | ○ |
| 3 | 5 | ○ | ○ | ○ | ○ | ○ | ○ | ○ | ○ | ○ | ○ | ○ | ○ |
| 3 | 8 | ○ | ○ | ○ | ○ | ○ | ○ | ○ | ○ | ○ | ○ | ○ | ○ |
| 3 | 10 | ○ | ○ | ○ | ○ | ○ | ○ | ○ | ○ | ○ | ○ | ○ | ○ |

TABLE 7

Confirmation Test for Stabilization Effects of Mixing with 1,1,1-trimethoxyethane

| 1,1,1-trimethoxy-ethane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 3 | 0.01 | X | X | ○ | X | X | ○ | X | X | ○ | X | X | ○ |
| 3 | 0.03 | X | X | ○ | X | X | ○ | X | X | ○ | X | X | ○ |
| 3 | 0.05 | ○ | ○ | ○ | ○ | ○ | ○ | ○ | ○ | ○ | ○ | ○ | ○ |
| 3 | 0.08 | ○ | ○ | ○ | ○ | ○ | ○ | ○ | ○ | ○ | ○ | ○ | ○ |
| 3 | 0.1 | ○ | ○ | ○ | ○ | ○ | ○ | ○ | ○ | ○ | ○ | ○ | ○ |
| 3 | 0.3 | ○ | ○ | ○ | ○ | ○ | ○ | ○ | ○ | ○ | ○ | ○ | ○ |
| 3 | 0.5 | ○ | ○ | ○ | ○ | ○ | ○ | ○ | ○ | ○ | ○ | ○ | ○ |
| 3 | 0.8 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 3 | 3 | ○ | ○ | ○ | ○ | ○ | ○ | ○ | ○ | ○ | ○ | ○ | ○ |
| 3 | 5 | ○ | ○ | ○ | ○ | ○ | ○ | ○ | ○ | ○ | ○ | ○ | ○ |
| 3 | 8 | ○ | ○ | ○ | ○ | ○ | ○ | ○ | ○ | ○ | ○ | ○ | ○ |
| 3 | 10 | ○ | ○ | ○ | ○ | ○ | ○ | ○ | ○ | ○ | ○ | ○ | ○ |

TABLE 8

Confirmation Test for Stabilization Effects of Mixing with 1,2-butylene oxide

| 1,2-butylene oxide adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 3 | 0.01 | X | X | ○ | X | X | ○ | X | X | ○ | X | X | ○ |
| 3 | 0.03 | X | X | ○ | X | X | ○ | X | X | ○ | X | X | ○ |
| 3 | 0.05 | ○ | ○ | ○ | ○ | ○ | ○ | ○ | ○ | ○ | ○ | ○ | ○ |
| 3 | 0.08 | ○ | ○ | ○ | ○ | ○ | ○ | ○ | ○ | ○ | ○ | ○ | ○ |
| 3 | 0.1 | ○ | ○ | ○ | ○ | ○ | ○ | ○ | ○ | ○ | ○ | ○ | ○ |
| 3 | 0.3 | ○ | ○ | ○ | ○ | ○ | ○ | ○ | ○ | ○ | ○ | ○ | ○ |
| 3 | 0.5 | ○ | ○ | ○ | ○ | ○ | ○ | ○ | ○ | ○ | ○ | ○ | ○ |
| 3 | 0.8 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 3 | 3 | ○ | ○ | ○ | ○ | ○ | ○ | ○ | ○ | ○ | ○ | ○ | ○ |
| 3 | 5 | ○ | ○ | ○ | ○ | ○ | ○ | ○ | ○ | ○ | ○ | ○ | ○ |
| 3 | 8 | ○ | ○ | ○ | ○ | ○ | ○ | ○ | ○ | ○ | ○ | ○ | ○ |
| 3 | 10 | ○ | ○ | ○ | ○ | ○ | ○ | ○ | ○ | ○ | ○ | ○ | ○ |

As shown in Table 3 and Table 0.4, in a case where nitromethane or nitroethane was mixed in addition to the stabilizers (A) to (D) and where the mixing amount of the stabilizers (A) to (D) was 0.05 parts by weight or more, generation of acidic gases was not observed, and it was determined that a more sufficient stabilization effect was imparted to n-propyl bromide. Moreover, as shown in Table 5 to Table 8, in a case where 1,3-dioxolane, trimethoxymethane, 1,1,1-trimethoxyethane or 1,2-butylene oxide was mixed in addition to the stabilizers (A) to (D) and where the mixing amount of the stabilizers (A) to (D) was 0.05 parts by weight or more, the conditions of the specimens and the test solutions were considerably favorable and generation of acidic gases was not observed, and so it was determined that a more sufficient stabilization effect was imparted to n-propyl bromide.

<Test 4>

Furthermore, a test was performed for examining appropriate mixing amounts of nitromethane, nitroethane, 1,3-dioxolane, trimethoxymethane, 1,1,1-trimethoxyethane and 1,2-butylene oxide. In this test, relative to 100 parts by weight of n-propyl bromide, the mixing amount of each of the stabilizers (A) to (D) was set to 0.05 parts by weight, and the mixing amount of nitromethane, nitroethane, 1,3-dioxolane, -trimethoxymethane, 1,1,1-trimethoxyethane or 1,2-butylene oxide was set within a range of 0.01 parts by weight to 10 parts by weight, to prepare test solutions. Then, 50 ml of the prepared test solutions were respectively poured into 100 ml glass Erlenmeyer flasks, and the same test was performed as the aforementioned test: the conditions of the aluminum specimens and the test solutions were respectively examined, and also the presence or absence of acidic gas generation was examined. As the stabilizers (A) to (D), "CELLOXIDE 2021P (CEL2021)" (product name), "CELLOXIDE 2081 (CEL2081)" (product name), "CELLOXIDE 2000 (CEL2000)" (product name) and "CELLOXIDE 3000 (CEL3000)" (product name) of DAICEL CHEMICAL INDUSTRIES LTD. were used, respectively.

Table 9 to Table 14 are the summaries of the test results.

Note that, the criterion for the condition of the aluminum specimen is set as "o; no change at all" and "x; luster is reduced." Moreover, the criterion for the condition of the test solution is set as "o; colorless and transparent" and "x; colored." Moreover, the presence or absence of the acidic gas generation is set as "o; no generation" and "x; presence of generation."

TABLE 9

Test of Examining Appropriate Mixing Amount of Nitroethane

| nitroethane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 0.01 | 0.05 | ○ | ○ | ○ | ○ | ○ | ○ | ○ | ○ | ○ | ○ | ○ | ○ |
| 0.05 | 0.05 | ○ | ○ | ○ | ○ | ○ | ○ | ○ | ○ | ○ | ○ | ○ | ○ |
| 0.08 | 0.05 | ○ | ○ | ○ | ○ | ○ | ○ | ○ | ○ | ○ | ○ | ○ | ○ |
| 0.1 | 0.05 | ○ | ○ | ○ | ○ | ○ | ○ | ○ | ○ | ○ | ○ | ○ | ○ |
| 0.2 | 0.05 | ○ | ○ | ○ | ○ | ○ | ○ | ○ | ○ | ○ | ○ | ○ | ○ |
| 0.3 | 0.05 | ○ | ○ | ○ | ○ | ○ | ○ | ○ | ○ | ○ | ○ | ○ | ○ |
| 0.5 | 0.05 | ○ | ○ | ○ | ○ | ○ | ○ | ○ | ○ | ○ | ○ | ○ | ○ |
| 0.8 | 0.05 | ○ | ○ | ○ | ○ | ○ | ○ | ○ | ○ | ○ | ○ | ○ | ○ |
| 1 | 0.05 | ○ | ○ | ○ | ○ | ○ | ○ | ○ | ○ | ○ | ○ | ○ | ○ |
| 3 | 0.05 | ○ | ○ | ○ | ○ | ○ | ○ | ○ | ○ | ○ | ○ | ○ | ○ |
| 5 | 0.05 | ○ | ○ | ○ | ○ | ○ | ○ | ○ | ○ | ○ | ○ | ○ | ○ |
| 8 | 0.05 | ○ | ○ | ○ | ○ | ○ | ○ | ○ | ○ | ○ | ○ | ○ | ○ |
| 10 | 0.05 | ○ | ○ | ○ | ○ | ○ | ○ | ○ | ○ | ○ | ○ | ○ | ○ |

TABLE 10

Test of Examining Appropriate Mixing Amount of Nitromethane

| nitromethane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 0.01 | 0.05 | ○ | ○ | ○ | ○ | ○ | ○ | ○ | ○ | ○ | ○ | ○ | ○ |
| 0.05 | 0.05 | ○ | ○ | ○ | ○ | ○ | ○ | ○ | ○ | ○ | ○ | ○ | ○ |
| 0.08 | 0.05 | ○ | ○ | ○ | ○ | ○ | ○ | ○ | ○ | ○ | ○ | ○ | ○ |
| 0.1 | 0.05 | ○ | ○ | ○ | ○ | ○ | ○ | ○ | ○ | ○ | ○ | ○ | ○ |
| 0.2 | 0.05 | ○ | ○ | ○ | ○ | ○ | ○ | ○ | ○ | ○ | ○ | ○ | ○ |
| 0.3 | 0.05 | ○ | ○ | ○ | ○ | ○ | ○ | ○ | ○ | ○ | ○ | ○ | ○ |
| 0.5 | 0.05 | ○ | ○ | ○ | ○ | ○ | ○ | ○ | ○ | ○ | ○ | ○ | ○ |
| 0.8 | 0.05 | ○ | ○ | ○ | ○ | ○ | ○ | ○ | ○ | ○ | ○ | ○ | ○ |
| 1 | 0.05 | ○ | ○ | ○ | ○ | ○ | ○ | ○ | ○ | ○ | ○ | ○ | ○ |
| 3 | 0.05 | ○ | ○ | ○ | ○ | ○ | ○ | ○ | ○ | ○ | ○ | ○ | ○ |
| 5 | 0.05 | ○ | ○ | ○ | ○ | ○ | ○ | ○ | ○ | ○ | ○ | ○ | ○ |
| 8 | 0.05 | ○ | ○ | ○ | ○ | ○ | ○ | ○ | ○ | ○ | ○ | ○ | ○ |
| 10 | 0.05 | ○ | ○ | ○ | ○ | ○ | ○ | ○ | ○ | ○ | ○ | ○ | ○ |

TABLE 11

Test of Examining Appropriate Mixing Amount of 1,3-dioxolane

| 1,3-dioxolane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 0.01 | 0.05 | X | X | X | X | X | X | X | X | X | X | X | X |
| 0.05 | 0.05 | ○ | ○ | ○ | ○ | ○ | ○ | ○ | ○ | ○ | ○ | ○ | ○ |
| 0.08 | 0.05 | ○ | ○ | ○ | ○ | ○ | ○ | ○ | ○ | ○ | ○ | ○ | ○ |
| 0.1 | 0.05 | ○ | ○ | ○ | ○ | ○ | ○ | ○ | ○ | ○ | ○ | ○ | ○ |
| 0.2 | 0.05 | ○ | ○ | ○ | ○ | ○ | ○ | ○ | ○ | ○ | ○ | ○ | ○ |
| 0.3 | 0.05 | ○ | ○ | ○ | ○ | ○ | ○ | ○ | ○ | ○ | ○ | ○ | ○ |
| 0.5 | 0.05 | ○ | ○ | ○ | ○ | ○ | ○ | ○ | ○ | ○ | ○ | ○ | ○ |
| 0.8 | 0.05 | ○ | ○ | ○ | ○ | ○ | ○ | ○ | ○ | ○ | ○ | ○ | ○ |

TABLE 11-continued

Test of Examining Appropriate Mixing Amount of 1,3-dioxolane

| 1,3-dioxolane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 1 | 0.05 | ○ | ○ | ○ | ○ | ○ | ○ | ○ | ○ | ○ | ○ | ○ | ○ |
| 3 | 0.05 | ○ | ○ | ○ | ○ | ○ | ○ | ○ | ○ | ○ | ○ | ○ | ○ |
| 5 | 0.05 | ○ | ○ | ○ | ○ | ○ | ○ | ○ | ○ | ○ | ○ | ○ | ○ |
| 8 | 0.05 | ○ | ○ | ○ | ○ | ○ | ○ | ○ | ○ | ○ | ○ | ○ | ○ |
| 10 | 0.05 | ○ | ○ | ○ | ○ | ○ | ○ | ○ | ○ | ○ | ○ | ○ | ○ |

TABLE 12

Test of Examining Appropriate Mixing Amount of Trimethoxymethane

| trimethoxy-methane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.01 | 0.05 | X | X | X | X | X | X | X | X | X | X | X | X |
| 0.05 | 0.05 | ○ | ○ | ○ | ○ | ○ | ○ | ○ | ○ | ○ | ○ | ○ | ○ |
| 0.08 | 0.05 | ○ | ○ | ○ | ○ | ○ | ○ | ○ | ○ | ○ | ○ | ○ | ○ |
| 0.1 | 0.05 | ○ | ○ | ○ | ○ | ○ | ○ | ○ | ○ | ○ | ○ | ○ | ○ |
| 0.2 | 0.05 | ○ | ○ | ○ | ○ | ○ | ○ | ○ | ○ | ○ | ○ | ○ | ○ |
| 0.3 | 0.05 | ○ | ○ | ○ | ○ | ○ | ○ | ○ | ○ | ○ | ○ | ○ | ○ |
| 0.5 | 0.05 | ○ | ○ | ○ | ○ | ○ | ○ | ○ | ○ | ○ | ○ | ○ | ○ |
| 0.8 | 0.05 | ○ | ○ | ○ | ○ | ○ | ○ | ○ | ○ | ○ | ○ | ○ | ○ |
| 1 | 0.05 | ○ | ○ | ○ | ○ | ○ | ○ | ○ | ○ | ○ | ○ | ○ | ○ |
| 3 | 0.05 | ○ | ○ | ○ | ○ | ○ | ○ | ○ | ○ | ○ | ○ | ○ | ○ |
| 5 | 0.05 | ○ | ○ | ○ | ○ | ○ | ○ | ○ | ○ | ○ | ○ | ○ | ○ |
| 8 | 0.05 | ○ | ○ | ○ | ○ | ○ | ○ | ○ | ○ | ○ | ○ | ○ | ○ |
| 10 | 0.05 | ○ | ○ | ○ | ○ | ○ | ○ | ○ | ○ | ○ | ○ | ○ | ○ |

TABLE 13

Test of Examining Appropriate Mixing Amount of 1,1,1-trimethoxyethane

| 1,1,1-trimethoxy-ethane adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.01 | 0.05 | X | X | X | X | X | X | X | X | X | X | X | X |
| 0.05 | 0.05 | ○ | ○ | ○ | ○ | ○ | ○ | ○ | ○ | ○ | ○ | ○ | ○ |
| 0.08 | 0.05 | ○ | ○ | ○ | ○ | ○ | ○ | ○ | ○ | ○ | ○ | ○ | ○ |
| 0.1 | 0.05 | ○ | ○ | ○ | ○ | ○ | ○ | ○ | ○ | ○ | ○ | ○ | ○ |
| 0.2 | 0.05 | ○ | ○ | ○ | ○ | ○ | ○ | ○ | ○ | ○ | ○ | ○ | ○ |
| 0.3 | 0.05 | ○ | ○ | ○ | ○ | ○ | ○ | ○ | ○ | ○ | ○ | ○ | ○ |
| 0.5 | 0.05 | ○ | ○ | ○ | ○ | ○ | ○ | ○ | ○ | ○ | ○ | ○ | ○ |
| 0.8 | 0.05 | ○ | ○ | ○ | ○ | ○ | ○ | ○ | ○ | ○ | ○ | ○ | ○ |
| 1 | 0.05 | ○ | ○ | ○ | ○ | ○ | ○ | ○ | ○ | ○ | ○ | ○ | ○ |
| 3 | 0.05 | ○ | ○ | ○ | ○ | ○ | ○ | ○ | ○ | ○ | ○ | ○ | ○ |
| 5 | 0.05 | ○ | ○ | ○ | ○ | ○ | ○ | ○ | ○ | ○ | ○ | ○ | ○ |
| 8 | 0.05 | ○ | ○ | ○ | ○ | ○ | ○ | ○ | ○ | ○ | ○ | ○ | ○ |
| 10 | 0.05 | ○ | ○ | ○ | ○ | ○ | ○ | ○ | ○ | ○ | ○ | ○ | ○ |

TABLE 14

Test of Examining Appropriate Mixing Amount of 1,2-butylene oxide

| 1,2-butylene oxide adding amount (part by weight) | adding amount (part by weight) | stabilizer (A) | | | stabilizer (B) | | | stabilizer (C) | | | stabilizer (D) | | |
|---|---|---|---|---|---|---|---|---|---|---|---|---|---|
| | | specimen condition | test-solution condition | presence/absence of gas generation | specimen condition | test solution condition | presence/absence of gas generation | specimen condition | test solution condition | presence/absence of gas generation | specimen condition | test solution condition | presence/absence of gas generation |
| 0.01 | 0.05 | X | X | X | X | X | X | X | X | X | X | X | X |
| 0.05 | 0.05 | ○ | ○ | ○ | ○ | ○ | ○ | ○ | ○ | ○ | ○ | ○ | ○ |
| 0.08 | 0.05 | ○ | ○ | ○ | ○ | ○ | ○ | ○ | ○ | ○ | ○ | ○ | ○ |
| 0.1 | 0.05 | ○ | ○ | ○ | ○ | ○ | ○ | ○ | ○ | ○ | ○ | ○ | ○ |
| 0.2 | 0.05 | ○ | ○ | ○ | ○ | ○ | ○ | ○ | ○ | ○ | ○ | ○ | ○ |
| 0.3 | 0.05 | ○ | ○ | ○ | ○ | ○ | ○ | ○ | ○ | ○ | ○ | ○ | ○ |
| 0.5 | 0.05 | ○ | ○ | ○ | ○ | ○ | ○ | ○ | ○ | ○ | ○ | ○ | ○ |
| 0.8 | 0.05 | ○ | ○ | ○ | ○ | ○ | ○ | ○ | ○ | ○ | ○ | ○ | ○ |
| 1 | 0.05 | ○ | ○ | ○ | ○ | ○ | ○ | ○ | ○ | ○ | ○ | ○ | ○ |
| 3 | 0.05 | ○ | ○ | ○ | ○ | ○ | ○ | ○ | ○ | ○ | ○ | ○ | ○ |
| 5 | 0.05 | ○ | ○ | ○ | ○ | ○ | ○ | ○ | ○ | ○ | ○ | ○ | ○ |
| 8 | 0.05 | ○ | ○ | ○ | ○ | ○ | ○ | ○ | ○ | ○ | ○ | ○ | ○ |
| 10 | 0.05 | ○ | ○ | ○ | ○ | ○ | ○ | ○ | ○ | ○ | ○ | ○ | ○ |

As shown in Table 9 and Table 10, when the mixing amount of nitromethane or nitroethane is set to 0.01 parts by weight or more, the conditions of the specimens and the test solutions were favorable and also there was no generation of acidic gases, and so it was confirmed that sufficient stabilization effects were obtained. On the other hand, as shown in Table 11 to Table 14, as for 1,3-dioxolane, trimethoxymethane, 1,1,1-trimethoxyethane or 1,2-butylene oxide, when the mixing amount is 0.01 parts by weight, the conditions of the specimens and the test solutions were poor and generation of acidic gases was observed, and thus favorable test results were not obtained. Meanwhile, in a case of 0.05 parts by weight or more, the conditions of the specimens and the test solutions were favorable and also there was no generation of acidic gases, and so it was confirmed that favorable test results were obtained.

From these, as for nitromethane and nitroethane, it was found that when the mixing amounts thereof were set to 0.01 parts by weight or more, further stabilization effects can be obtained. Moreover, as for 1,3-dioxolane, trimethoxymethane, 1,1,1-trimethoxyethane and 1,2-butylene oxide, it was found that when the mixing amounts were set to 0.05 parts by weight or more, further stabilization effects can be obtained.

<Test 5>

Next, a test was performed for examining the influences on iron and copper. In this test, relative to 100 parts by weight of n-propyl bromide, the mixing amounts of the stabilizers (A) to (D) were set within a range of 0.001 parts by weight to 10 parts by weight, to prepare, test solutions. Then, 50 ml of the prepared test solutions were respectively poured into 100 ml glass Erlenmeyer flasks, and an iron specimen or a copper specimen (both dimensions: 13 mm×65 mm×3 mm), whose surfaces were well polished and which were cleaned and dried sufficiently, were respectively placed therein so as to extend over both the gaseous and liquid phases. Subsequently, a reflux condenser was attached to the top portion of the Erlenmeyer flask, and the solution was heated up to the boiling point on a hot water bath and refluxed while bringing the specimen into contact with both the gaseous and liquid phases. A pH test paper was attached to the reflux condenser. After heat-refluxing for 140 hours, the solution was cooled to room temperature, the specimen was taken out, and then the corrosion condition and coloring condition of the liquid phase were observed. Furthermore, the generated acidic gases were confirmed by the pH test paper. As the stabilizers (A) to (D), "CELLOXIDE 2021P (CEL2021)" (product name), "CELLOXIDE 2081 (CEL2081)" (product name), "CELLOXIDE 2000 (CEL2000)" (product name) and "CELLOXIDE 3000 (CEL3000)" (product name) of DAICEL CHEMICAL INDUSTRIES LTD. were used, respectively.

Table 15 and Table 16 are the summaries of the test results. Table 15 shows the test results for iron. Table 16 shows the test results for copper. Note that, the criterion for the condition of the iron specimen or the copper specimen is set as "o; no change at all" and "x; luster is reduced." Moreover, the criterion for the condition of the test solution is set as "o; colorless and transparent" and "x; remarkably colored." Moreover, the presence or absence of the acidic gas generation is set as "o; no generation" and "x; presence of generation."

TABLE 15

Confirmation Test for Influence on Iron

| adding amount (part by weight) | stabilizer (A) | | | stabilizer (B) | | | stabilizer (C) | | | stabilizer (D) | | |
|---|---|---|---|---|---|---|---|---|---|---|---|---|
| | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 0.001 | X | X | X | X | X | X | X | X | X | X | X | X |
| 0.005 | X | X | X | X | X | X | X | X | X | X | X | X |
| 0.01 | X | X | X | X | X | X | X | X | X | X | X | X |

TABLE 15-continued

Confirmation Test for Influence on Iron

| adding amount (part by weight) | stabilizer (A) | | | stabilizer (B) | | | stabilizer (C) | | | stabilizer (D) | | |
|---|---|---|---|---|---|---|---|---|---|---|---|---|
| | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.05 | X | X | X | X | X | X | X | X | X | X | X | X |
| 0.08 | X | X | X | X | X | X | X | X | X | X | X | X |
| 0.1 | ◯ | ◯ | ◯ | ◯ | ◯ | ◯ | ◯ | ◯ | ◯ | ◯ | ◯ | ◯ |
| 0.3 | ◯ | ◯ | ◯ | ◯ | ◯ | ◯ | ◯ | ◯ | ◯ | ◯ | ◯ | ◯ |
| 0.5 | ◯ | ◯ | ◯ | ◯ | ◯ | ◯ | ◯ | ◯ | ◯ | ◯ | ◯ | ◯ |
| 0.8 | ◯ | ◯ | ◯ | ◯ | ◯ | ◯ | ◯ | ◯ | ◯ | ◯ | ◯ | ◯ |
| 1 | ◯ | ◯ | ◯ | ◯ | ◯ | ◯ | ◯ | ◯ | ◯ | ◯ | ◯ | ◯ |
| 3 | ◯ | ◯ | ◯ | ◯ | ◯ | ◯ | ◯ | ◯ | ◯ | ◯ | ◯ | ◯ |
| 5 | ◯ | ◯ | ◯ | ◯ | ◯ | ◯ | ◯ | ◯ | ◯ | ◯ | ◯ | ◯ |
| 8 | ◯ | ◯ | ◯ | ◯ | ◯ | ◯ | ◯ | ◯ | ◯ | ◯ | ◯ | ◯ |
| 10 | ◯ | ◯ | ◯ | ◯ | ◯ | ◯ | ◯ | ◯ | ◯ | ◯ | ◯ | ◯ |

TABLE 16

Confirmation Test for Influence on Copper

| adding amount (part by weight) | stabilizer (A) | | | stabilizer (B) | | | stabilizer (C) | | | stabilizer (D) | | |
|---|---|---|---|---|---|---|---|---|---|---|---|---|
| | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.001 | X | X | X | X | X | X | X | X | X | X | X | X |
| 0.005 | X | X | X | X | X | X | X | X | X | X | X | X |
| 0.01 | X | X | X | X | X | X | X | X | X | X | X | X |
| 0.05 | X | X | X | X | X | X | X | X | X | X | X | X |
| 0.08 | X | X | X | X | X | X | X | X | X | X | X | X |
| 0.1 | ◯ | ◯ | ◯ | ◯ | ◯ | ◯ | ◯ | ◯ | ◯ | ◯ | ◯ | ◯ |
| 0.3 | ◯ | ◯ | ◯ | ◯ | ◯ | ◯ | ◯ | ◯ | ◯ | ◯ | ◯ | ◯ |
| 0.5 | ◯ | ◯ | ◯ | ◯ | ◯ | ◯ | ◯ | ◯ | ◯ | ◯ | ◯ | ◯ |
| 0.8 | ◯ | ◯ | ◯ | ◯ | ◯ | ◯ | ◯ | ◯ | ◯ | ◯ | ◯ | ◯ |
| 1 | ◯ | ◯ | ◯ | ◯ | ◯ | ◯ | ◯ | ◯ | ◯ | ◯ | ◯ | ◯ |
| 3 | ◯ | ◯ | ◯ | ◯ | ◯ | ◯ | ◯ | ◯ | ◯ | ◯ | ◯ | ◯ |
| 5 | ◯ | ◯ | ◯ | ◯ | ◯ | ◯ | ◯ | ◯ | ◯ | ◯ | ◯ | ◯ |
| 8 | ◯ | ◯ | ◯ | ◯ | ◯ | ◯ | ◯ | ◯ | ◯ | ◯ | ◯ | ◯ |
| 10 | ◯ | ◯ | ◯ | ◯ | ◯ | ◯ | ◯ | ◯ | ◯ | ◯ | ◯ | ◯ |

As shown in Table 15 and Table 16, as in the case of aluminum, when the mixing amounts of the stabilizers (A) to (D) were set to 0.001 parts by weight to 0.08 parts by weight relative to 100 parts by weight of n-propyl bromide, the conditions of the specimens and the test solutions were poor and generation of acidic gases was observed, and so it was determined that a sufficient stabilization effect was not imparted to n-propyl bromide. On the other hand, in a case where the mixing amounts of the stabilizers (A) to (D) were 0.1 parts by weight or more relative to 100 parts by weight of n-propyl bromide, the conditions of the specimens and the test solutions were favorable and generation of acidic gases was not observed, and so it was determined that a sufficient stabilization effect was imparted to n-propyl bromide. From this, as for iron and copper, it was found that the mixing amounts of stabilizers (A) to (D) need to be set to 0.1 parts by weight or more.

<Test 6>

Next, description will be given of a test for confirming the effect of preventing rust occurrence on metallic components or the like by mixing the stabilizers (A) to (D) in a case where the cleaning solvent is repeatedly used for vapor degreasing, for example.

Here, first, a test was performed for examining the mixing amounts of 1,3-dioxolane, trimethoxymethane, 1,1,1-trimethoxyethane and 1,2-butylene oxide. In this test, each test solution was prepared by mixing, relative to 100 parts by weight of n-propyl bromide, 1 part by weight of nitromethane or nitroethane and 0.01 parts by weight to 10 parts by weight of 1,3-dioxolane, trimethoxymethane, 1,1,1-trimethoxyethane or 1,2-butylene oxide. Then, 50 ml of the prepared test solutions were respectively poured into 100 ml glass Erlenmeyer flasks, and aluminum specimens (specification: JIS A-1000P, dimension: 13 mm×65 mm×3 mm), whose surfaces were well polished and which were cleaned and dried sufficiently, were respectively placed therein so as to extend over both the gaseous and liquid phases. Subsequently, a reflux condenser was attached to the top portion of the Erlenmeyer flask, and the solution was heated up to the boiling point on a hot water bath and refluxed while bringing the specimen into contact with both the gaseous and liquid phases. A pH test paper was attached to the reflux condenser. After heat-refluxing for 140 hours, the solution was cooled to room temperature, the specimen was taken out, and then the corrosion condition and coloring condition of the liquid phase were observed. Furthermore, the generated acidic gases were confirmed by the pH test paper.

Table 17 and Table 18 are the summaries of the test results. Table 17 shows the test results for nitromethane, and Table 18 shows the test results for nitroethane. Note that, the criterion for the condition of the aluminum specimen is set as "o; no change at all" and "x; luster is reduced." Moreover, the criterion for the condition of the test solution is set as "o; colorless and transparent" and "x; colored." Moreover, the presence or absence of the acidic gas generation is set as "o; no generation" and "x; presence of generation."

Next, a test was performed for examining the mixing amounts of nitromethane and nitroethane. In this test, each test solution was prepared by mixing, relative to 100 parts by weight of n-propyl bromide, 0.01 parts by weight to 10 parts by weight of nitromethane or nitroethane and 1 part by weight of 1,3-dioxolane, trimethoxymethane, 1,1,1-trimethoxyethane or 1,2-butylene oxide. Then, 50 ml of the prepared test solutions were respectively poured into 100 ml glass Erlenmeyer flasks, and the same test was performed as the aforementioned case. After heat-refluxing for 140 hours, the solution was cooled to room temperature, the specimen was taken out, and then the corrosion condition and coloring condition

TABLE 17

Confirmation Test for Stabilization Effects of Mixing Nitromethane with Each Stabilizer

| nitromethane adding amount (part by weight) | adding amount (part by weight) | 1,3-dioxolane | | | trimethoxymethane | | | 1,1,1-trimethoxyethane | | | 1,2-butylene oxide | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 1 | 0.01 | ○ | ○ | X | ○ | ○ | X | ○ | ○ | X | ○ | ○ | X |
| 1 | 0.03 | ○ | ○ | X | ○ | ○ | X | ○ | ○ | X | ○ | ○ | X |
| 1 | 0.05 | ○ | ○ | X | ○ | ○ | X | ○ | ○ | X | ○ | ○ | X |
| 1 | 0.08 | ○ | ○ | X | ○ | ○ | X | ○ | ○ | X | ○ | ○ | X |
| 1 | 0.1 | ○ | ○ | ○ | ○ | ○ | ○ | ○ | ○ | ○ | ○ | ○ | ○ |
| 1 | 0.3 | ○ | ○ | ○ | ○ | ○ | ○ | ○ | ○ | ○ | ○ | ○ | ○ |
| 1 | 0.5 | ○ | ○ | ○ | ○ | ○ | ○ | ○ | ○ | ○ | ○ | ○ | ○ |
| 1 | 0.8 | ○ | ○ | ○ | ○ | ○ | ○ | ○ | ○ | ○ | ○ | ○ | ○ |
| 1 | 1 | ○ | ○ | ○ | ○ | ○ | ○ | ○ | ○ | ○ | ○ | ○ | ○ |
| 1 | 3 | ○ | ○ | ○ | ○ | ○ | ○ | ○ | ○ | ○ | ○ | ○ | ○ |
| 1 | 5 | ○ | ○ | ○ | ○ | ○ | ○ | ○ | ○ | ○ | ○ | ○ | ○ |
| 1 | 8 | ○ | ○ | ○ | ○ | ○ | ○ | ○ | ○ | ○ | ○ | ○ | ○ |
| 1 | 10 | ○ | ○ | ○ | ○ | ○ | ○ | ○ | ○ | ○ | ○ | ○ | ○ |

TABLE 18

Confirmation Test for Stabilization Effects of Mixing Nitroethane with Each Stabilizer

| nitroethane adding amount (part by weight) | adding amount (part by weight) | 1,3-dioxolane | | | trimethoxymethane | | | 1,1,1-trimethoxyethane | | | 1,2-butylene oxide | | |
|---|---|---|---|---|---|---|---|---|---|---|---|---|---|
| | | specimen condition | test solution condition | presence/absence of gas generation | specimen condition | test solution condition | presence/absence of gas generation | specimen condition | test solution condition | presence/absence of gas generation | specimen condition | test solution condition | presence/absence of gas generation |
| 1 | 0.01 | ○ | ○ | X | ○ | ○ | X | ○ | ○ | X | ○ | ○ | X |
| 1 | 0.03 | ○ | ○ | X | ○ | ○ | X | ○ | ○ | X | ○ | ○ | X |
| 1 | 0.05 | ○ | ○ | X | ○ | ○ | X | ○ | ○ | X | ○ | ○ | X |
| 1 | 0.08 | ○ | ○ | X | ○ | ○ | X | ○ | ○ | X | ○ | ○ | X |
| 1 | 0.1 | ○ | ○ | ○ | ○ | ○ | ○ | ○ | ○ | ○ | ○ | ○ | ○ |
| 1 | 0.3 | ○ | ○ | ○ | ○ | ○ | ○ | ○ | ○ | ○ | ○ | ○ | ○ |
| 1 | 0.5 | ○ | ○ | ○ | ○ | ○ | ○ | ○ | ○ | ○ | ○ | ○ | ○ |
| 1 | 0.8 | ○ | ○ | ○ | ○ | ○ | ○ | ○ | ○ | ○ | ○ | ○ | ○ |
| 1 | 1 | ○ | ○ | ○ | ○ | ○ | ○ | ○ | ○ | ○ | ○ | ○ | ○ |
| 1 | 3 | ○ | ○ | ○ | ○ | ○ | ○ | ○ | ○ | ○ | ○ | ○ | ○ |
| 1 | 5 | ○ | ○ | ○ | ○ | ○ | ○ | ○ | ○ | ○ | ○ | ○ | ○ |
| 1 | 8 | ○ | ○ | ○ | ○ | ○ | ○ | ○ | ○ | ○ | ○ | ○ | ○ |
| 1 | 10 | ○ | ○ | ○ | ○ | ○ | ○ | ○ | ○ | ○ | ○ | ○ | ○ |

As shown in Table 17 and Table 18, in both cases of nitromethane and nitroethane, when the mixing amounts of 1,3-dioxolane, trimethoxymethane, 1,1,1-trimethoxyethane and 1,2-butylene oxide were 0.1 parts by weight to 10 parts by weight, the conditions of the specimens and the test solutions were favorable and there was no generation of gases, and so it was confirmed that sufficient stabilization effects were obtained.

of the liquid phase were observed. Furthermore, the generated acidic gases were confirmed by the pH test paper.

Table 19 and Table 20 are the summaries of the test results. Table 19 shows the test results for nitromethane, and Table 20 shows the test results for nitroethane. Note that, the criterion for the condition of the aluminum specimen is set as "o; no change at all" and "x; luster is reduced." Moreover, the criterion for the condition of the test solution is set as "o; colorless and transparent" and "x; colored." Moreover, the presence or absence of the acidic gas generation is set as "o; no generation" and "x; presence of generation."

on a metal piece (here, an iron piece) in a case where the cleaning solvent was repeatedly used for vapor degreasing, for example.

TABLE 19

Test of Examining Appropriate Mixing Amounts of Nitromethane

| nitromethane adding amount (part by weight) | adding amount (part by weight) | 1,3-dioxolane | | | trimethoxymethane | | | 1,1,1-trimethoxyethane | | | 1,2-butylene oxide | | |
|---|---|---|---|---|---|---|---|---|---|---|---|---|---|
| | | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.01 | 1 | X | X | ○ | X | X | ○ | X | X | ○ | X | X | ○ |
| 0.03 | 1 | X | X | ○ | X | X | ○ | X | X | ○ | X | X | ○ |
| 0.05 | 1 | X | X | ○ | X | X | ○ | X | X | ○ | X | X | ○ |
| 0.08 | 1 | X | X | ○ | X | X | ○ | X | X | ○ | X | X | ○ |
| 0.1 | 1 | ○ | ○ | ○ | ○ | ○ | ○ | ○ | ○ | ○ | ○ | ○ | ○ |
| 0.3 | 1 | ○ | ○ | ○ | ○ | ○ | ○ | ○ | ○ | ○ | ○ | ○ | ○ |
| 0.5 | 1 | ○ | ○ | ○ | ○ | ○ | ○ | ○ | ○ | ○ | ○ | ○ | ○ |
| 0.8 | 1 | ○ | ○ | ○ | ○ | ○ | ○ | ○ | ○ | ○ | ○ | ○ | ○ |
| 1 | 1 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 5 | 1 | ○ | ○ | ○ | ○ | ○ | ○ | ○ | ○ | ○ | ○ | ○ | ○ |
| 8 | 1 | ○ | ○ | ○ | ○ | ○ | ○ | ○ | ○ | ○ | ○ | ○ | ○ |
| 10 | 1 | ○ | ○ | ○ | ○ | ○ | ○ | ○ | ○ | ○ | ○ | ○ | ○ |

TABLE 20

Test of Examining Appropriate Mixing Amounts of Nitroethane

| nitroethane adding amount (part by weight) | adding amount (part by weight) | 1,3-dioxolane | | | trimethoxymethane | | | 1,1,1-trimethoxyethane | | | 1,2-butylene oxide | | |
|---|---|---|---|---|---|---|---|---|---|---|---|---|---|
| | | specimen condition | test solution condition | presence/ absence of gas generation | specimen condition | test solution condition | presence/ absence of gas generation | specimen condition | test solution condition | presence/ absence of gas generation | specimen condition | test solution condition | presence/ absence of gas generation |
| 0.01 | 1 | X | X | ○ | X | X | ○ | X | X | ○ | X | X | ○ |
| 0.03 | 1 | X | X | ○ | X | X | ○ | X | X | ○ | X | X | ○ |
| 0.05 | 1 | X | X | ○ | X | X | ○ | X | X | ○ | X | X | ○ |
| 0.08 | 1 | X | X | ○ | X | X | ○ | X | X | ○ | X | X | ○ |
| 0.1 | 1 | ○ | ○ | ○ | ○ | ○ | ○ | ○ | ○ | ○ | ○ | ○ | ○ |
| 0.3 | 1 | ○ | ○ | ○ | ○ | ○ | ○ | ○ | ○ | ○ | ○ | ○ | ○ |
| 0.5 | 1 | ○ | ○ | ○ | ○ | ○ | ○ | ○ | ○ | ○ | ○ | ○ | ○ |
| 0.8 | 1 | ○ | ○ | ○ | ○ | ○ | ○ | ○ | ○ | ○ | ○ | ○ | ○ |
| 1 | 1 | ○ | ○ | ○ | ○ | ○ | ○ | ○ | ○ | ○ | ○ | ○ | ○ |
| 3 | 1 | ○ | ○ | ○ | ○ | ○ | ○ | ○ | ○ | ○ | ○ | ○ | ○ |
| 5 | 1 | ○ | ○ | ○ | ○ | ○ | ○ | ○ | ○ | ○ | ○ | ○ | ○ |
| 8 | 1 | ○ | ○ | ○ | ○ | ○ | ○ | ○ | ○ | ○ | ○ | ○ | ○ |
| 10 | 1 | ○ | ○ | ○ | ○ | ○ | ○ | ○ | ○ | ○ | ○ | ○ | ○ |

As shown in Table 19 and Table 20, in the respective cases of 1,3-dioxolane, trimethoxymethane, 1,1,1-trimethoxyethane and 1,2-butylene oxide, when the mixing amount of nitromethane or nitroethane was 0.1 parts by weight to 10 parts by weight, the conditions of the specimens and the test solutions were favorable and there was no generation of gases, and so it was confirmed that sufficient stabilization effects were obtained.

<Test 7>

Next, a test was performed for confirming stabilization effects obtained by mixing of the stabilizers (A) to (D). Here, a test was performed for examining whether or not rust occurs As the stabilizer (A) [3,4-epoxycyclohexenylmethyl 3',4'-epoxycyclohexene carboxylate], "CELLOXIDE 2021P (CEL2021)" (product name) of DAICEL CHEMICAL INDUSTRIES LTD. was used. Moreover, as the stabilizer (B) [ε-caprolactone modified 3,4-epoxycyclohexylmethyl 3',4'-epoxycyclohexane carboxylate], "CELLOXIDE 2081 (CEL2081)" (product name) of DAICEL CHEMICAL INDUSTRIES LTD. was used. Moreover, as the stabilizer (C) {vinylcyclohexene monoxide [1,2-epoxy-4-vinylcyclohexane]}, "CELLOXIDE 2000 (CEL2000)" (product name) of DAICEL CHEMICAL INDUSTRIES LTD. was used. Moreover, as the stabilizer (D) [1,2:8,9-diepoxylimonene], "CEL- LOXIDE 3000 (CEL3000)" (product name) of DAICEL CHEMICAL INDUSTRIES LTD. was used.

In this test, first, each test solution was prepared by mixing, relative to 100 parts by weight of n-propyl bromide, 1 part by weight of nitromethane or nitroethane, 1 part by weight of 1,3-dioxolane, trimethoxymethane, 1,1,1-trimethoxyethane or 1,2-butylene oxide, and further, 0.001 parts by weight to 10 parts by weight of each stabilizer (A) to (D). Moreover, test solutions without the stabilizers (A) to (D) were also prepared. Then, 50 ml of the prepared test solutions were respectively poured into 100 ml glass Erlenmeyer flasks, a reflux condenser was attached to the top portion of the Erlenmeyer flask, the solution was heated up to the boiling point on a hot water bath, and after heat-refluxing for 140 hours, the solution was cooled to room temperature. Subsequently, an iron piece (specification: JIS G3303, dimension: 13 mm×65 mm×3 mm), whose surfaces were well polished with a sand paper (No. 100), was placed as a test piece into each test solution in the Erlenmeyer flask and immersed therein at normal temperature for 140 hours, and the presence or absence of rust occurrence was observed.

Table 21 to Table 28 are the summaries of the test results. Note that "x" represents a case where rust occurred, and "o" represents a case where rust did not occur.

[Table 21]

TABLE 21

Test of Examining Appropriate Mixing Amounts of Stabilizers (A) to (D)

| nitromethane (part by weight) | 1,2-butylene oxide (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 22]

TABLE 22

Test of Examining Appropriate Mixing Amounts of Stabilizers (A) to (D)

| nitroethane (part by weight) | 1,2-butylene oxide (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 23]

TABLE 23

Test of Examining Appropriate Mixing Amounts of Stabilizers (A) to (D)

| nitromethane (part by weight) | 1,3-dioxolane (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 24]

TABLE 24

Test of Examining Appropriate Mixing Amounts of Stabilizers (A) to (D)

| nitroethane (part by weight) | 1,3-dioxolane (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 25]

TABLE 25

Test of Examining Appropriate Mixing Amounts of Stabilizers (A) to (D)

| nitromethane (part by weight) | trimethoxy-methane (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |

TABLE 25-continued

Test of Examining Appropriate Mixing Amounts of Stabilizers (A) to (D)

| nitromethane (part by weight) | trimethoxy-methane (part by weight) | adding amount (part by weight) | stabilizer (A) | stabilizer (B) | stabilizer (C) | stabilizer (D) |
|---|---|---|---|---|---|---|
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 26]

TABLE 26

Test of Examining Appropriate Mixing Amounts of Stabilizers (A) to (D)

| nitroethane (part by weight) | trimethoxy-methane (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 27]

TABLE 27

Test of Examining Appropriate Mixing Amounts of Stabilizers (A) to (D)

| nitromethane (part by weight) | 1,1,1-trimethoxy-ethane (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

[Table 28]

TABLE 28

Test of Examining Appropriate Mixing Amounts of Stabilizers (A) to (D)

| nitroethane (part by weight) | 1,1,1-trimethoxy-ethane (part by weight) | adding amount (part by weight) | stabilizer (A) | stabilizer (B) | stabilizer (C) | stabilizer (D) |
|---|---|---|---|---|---|---|
| 1 | 1 | 0 | X | X | X | X |
| 1 | 1 | 0.001 | X | X | X | X |
| 1 | 1 | 0.005 | ○ | ○ | ○ | ○ |
| 1 | 1 | 0.01 | ○ | ○ | ○ | ○ |
| 1 | 1 | 0.05 | ○ | ○ | ○ | ○ |
| 1 | 1 | 0.08 | ○ | ○ | ○ | ○ |
| 1 | 1 | 0.1 | ○ | ○ | ○ | ○ |
| 1 | 1 | 0.3 | ○ | ○ | ○ | ○ |
| 1 | 1 | 0.5 | ○ | ○ | ○ | ○ |
| 1 | 1 | 0.8 | ○ | ○ | ○ | ○ |
| 1 | 1 | 1 | ○ | ○ | ○ | ○ |
| 1 | 1 | 3 | ○ | ○ | ○ | ○ |
| 1 | 1 | 5 | ○ | ○ | ○ | ○ |
| 1 | 1 | 8 | ○ | ○ | ○ | ○ |
| 1 | 1 | 10 | ○ | ○ | ○ | ○ |

As shown in Table 21 to Table 28, in a case where the mixing amounts of the stabilizers (A) to (D) were 0.001 parts by weight, the occurrence of rust was observed. Meanwhile, in a case where the mixing amounts of stabilizers (A) to (D) were 0.005 parts by weight to 10 parts by weight, the occurrence of rust was not observed, and the mixing amounts were confirmed to be favorable.

The invention claimed is:

1. A normal propyl bromide composition including, relative to 100 parts by weight of normal propyl bromide, 0.1 parts by weight to 10 parts by weight of at least one stabilizer selected from the following (A) to (D):
(A) 3,4-epoxycyclohexenylmethyl 3',4'-epoxycyclohexene carboxylate;
(B) ε-caprolactone modified 3,4-epoxycyclohexylmethyl 3',4'-epoxycyclohexane carboxylate;
(C) vinylcyclohexene monoxide; and
(D) 1,2:8,9-diepoxylimonene.

2. A normal propyl bromide composition including, relative to 100 parts by weight of normal propyl bromide:
0.05 parts by weight to 10 parts by weight of at least one stabilizer selected from nitromethane, nitroethane, 1,3-dioxolane, trimethoxymethane, 1,1,1-trimethoxyethane and 1,2-butylene oxide; and
0.05 parts by weight to 10 parts by weight of at least one stabilizer selected from the following (A) to (D):
(A) 3,4-epoxycyclohexenylmethyl 3',4'-epoxycyclohexene carboxylate;
(B) ε-caprolactone modified 3,4-epoxycyclohexylmethyl 3',4'-epoxycyclohexane carboxylate;
(C) vinylcyclohexene monoxide; and
(D) 1,2:8,9-diepoxylimonene.

3. A normal propyl bromide composition including, relative to 100 parts by weight of normal propyl bromide:
0.01 parts by weight to 10 parts by weight of at least either one stabilizer of nitromethane and nitroethane; and
0.05 parts by weight to 10 parts by weight of at least one stabilizer selected from the following (A) to (D):
(A) 3,4-epoxycyclohexenylmethyl 3',4'-epoxycyclohexene carboxylate;
(B) ε-caprolactone modified 3,4-epoxycyclohexylmethyl 3',4'-epoxycyclohexane carboxylate;
(C) vinylcyclohexene monoxide; and
(D) 1,2:8,9-diepoxylimonene.

4. A normal propyl bromide composition including, relative to 100 parts by weight of normal propyl bromide:
0.1 parts by weight to 10 parts by weight of at least either one stabilizer of nitromethane and nitroethane;
0.1 parts by weight to 10 parts by weight of at least one stabilizer selected from 1,3-dioxolane, trimethoxymethane, 1,1,1-trimethoxyethane and 1,2-butylene oxide; and
0.005 parts by weight to 10 parts by weight of at least one stabilizer selected from the following (A) to (D):
(A) 3,4-epoxycyclohexenylmethyl 3',4'-epoxycyclohexene carboxylate;
(B) ε-caprolactone modified 3,4-epoxycyclohexylmethyl 3',4'-epoxycyclohexane carboxylate;
(C) vinylcyclohexene monoxide; and
(D) 1,2:8,9-diepoxylimonene.

* * * * *